US00PP13048P2

(12) United States Plant Patent
van Rijsselberghe

(10) Patent No.: US PP13,048 P2
(45) Date of Patent: Oct. 1, 2002

(54) PHALAENOPSIS PLANT NAMED 'ARTEMISA'

(75) Inventor: Ronie van Rijsselberghe, Lochristi (BE)

(73) Assignee: MicroFlon N.V., Lochristi (BE)

( * ) Notice: Subject to any disclaimer, the term of this patent is extended or adjusted under 35 U.S.C. 154(b) by 0 days.

(21) Appl. No.: 09/797,254

(22) Filed: Mar. 1, 2001

(51) Int. Cl.[7] ..... A01H 5/00

(52) U.S. Cl. ..... Plt./311

(58) Field of Search ..... Plt./311

(56) References Cited

PUBLICATIONS

UPOV–ROM GTITM Computer Database 2001/06, 2001, GTI Jouve Retrieval Software, Citation for Phalaenopsis 'Artemis'.*

Curtis, Charles H., Orchids Their Description and Cultivation, 1950, Putman & Company, Ltd., p. 159.*

* cited by examiner

*Primary Examiner*—Bruce R. Campell
*Assistant Examiner*—June Hwu
(74) *Attorney, Agent, or Firm*—C. A. Whealy

(57) ABSTRACT

A new and distinct cultivar of Phalaenopsis plant named 'Artemisa', characterized by its upright and compact plant habit with relatively short flower stems; short dark green leaves; showy purple-colored flowers; freely flowering habit; and excellent flower longevity.

2 Drawing Sheets

BOTANICAL CLASSIFICATION

Phalaenopsis hybrid cultivar Artemisa.

BACKGROUND OF THE INVENTION

The present invention relates to a new and distinct cultivar of Phalaenopsis, botanically known as Phalaenopsis hybrid and hereinafter referred to by the name 'Artemisa'.

The new Phalaenopsis is a product of a planned breeding program conducted by the Inventor in Lochristi, Belgium. The objective of the breeding program is to create new compact Phalaenopsis cultivars.

The new Phalaenopsis originated from a cross made by the Inventor in June, 1994, in Lochristi, Belgium, of a proprietary Phalaenopsis hybrid selection identified as MFB001 as the female, or seed, parent with a proprietary Phalaenopsis hybrid selection identified as MFR035 as the male, or pollen, parent.

The new Phalaenopsis was discovered and selected by the Inventor as a flowering plant within the progeny of the stated cross in a controlled environment in Lochristi, Belgium. The selection of this plant was based on its compact plant habit and purple flowers.

Asexual reproduction of the new Phalaenopsis by tissue culture in a controlled environment in Lochristi, Belgium, has shown that the unique features of this new phalaenopsis are stable and reproduced true to type in successive generations.

BRIEF SUMMARY OF THE INVENTION

The new Phalaenopsis has not been observed under all possible environmental conditions. The phenotype may vary somewhat with variations in environment such as temperature, daylength, light intensity, nutritional and water status without, however, any variance in genotype.

The following traits have been repeatedly observed and are determined to be the unique characteristics of 'Artemisa'. These characteristics in combination distinguish 'Artemisa' as a new and distinct cultivar:

1. Upright and compact plant habit with relatively short flower stems.
2. Short dark green leaves.
3. Showy purple-colored flowers.
4. Freely flowering, about 10 to 15 flowers and flower buds per raceme.
5. Excellent flower longevity, flowers last about 8 weeks on the plant.

Plants of the new Phalaenopsis can be compared to plants of the female parent, the selection MRB001. In side-by-side comparisons conducted in Lochristi, Belgium, plants of the new Phalaenopsis are more compact, have shorter flowering stems and have more rounded leaf apices than plants of the selection MRB001. Plants of the new Phalaenopsis can be compared to plants of the white-flowered male parent, the selection MFR035. In side-by-side comparisons conducted in Lochristi, Belgium, plants of the new Phalaenopsis have darker green leaves than plants of the selection MFR035.

BRIEF DESCRIPTION OF THE PHOTOGRAPHS

The accompanying colored photographs illustrate the overall appearance of the new Phalaenopsis, showing the colors as true as it is reasonably possible to obtain in colored reproductions of this type. Colors in the photographs may differ slightly from the color values cited in the detailed botanical description, which accurately describe the colors of the new Phalaenopsis.

The photograph at the top of the first sheet comprises a side perspective view of a typical plant of 'Artemisa'.

The photograph at the bottom of the first sheet is a close-up view of typical leaves of 'Artemisa'.

The photograph at the top of the second sheet comprises a close-up view of a typical inflorescence of 'Artemisa'.

The photograph at the bottom of the second sheet is a close-up view of typical flowers and flower buds of 'Artemisa'. Plants in the photographs were about 45 weeks from planting.

DETAILED BOTANICAL DESCRIPTION

The aforementioned and following observations, measurements, values, and comparisons describe plants grown in Lochristi, Belgium, in a glass-covered greenhouse in 13-cm containers under conditions which approximate commerical Phalaenopsis production conditions. Plants were grown for about 45 weeks after planting. During the first 25 weeks of production, day and night temperatures averaged 25° C.; during the next four weeks of production, day and night temperatures averaged 18° C.; and for the last weeks of production, day and night temperatures averaged 22° C. In the following description, color references are made to The Royal Horticultural Society Colour Chart except where general terms of ordinary dictionary significance are used.

Parentage:

*Female or seed parent*.—Proprietary selection of Phalaenopsis hybrid identified as MFB001, not patented.

*Male or pollen parent*.—Proprietary selection of Phalaenopsis hybrid identified as MFR035, not patented.

Propagation:

*Type*.—By tissue culture.

*Time to initiate roots on a tissue-cultured plantlet*.—Summer: About 28 days at temperatures of 24° C. Winter: About 42 days at temperatures of 24° C.

*Time to produce to develop a rooted plant from a tissue-cultured plantlet*.—Summer: About 168 days at temperatures of 24° C. Winter: About 270 days at temperatures of 24° C.

*Root description*.—Thick, fleshy, rounded, slightly glossy; about 5 mm in diameter; 138A to 143A in color.

Plant description:

*Plant form and growth habit*.—Monopodial epiphyte; upright and compact plant habit. Appropriate for 13-cm containers.

*Growth rate*.—During the summer in Northern Europe, one leaf is formed about every seven weeks; during the winter in Northern Europe, one leaf is formed about every nine weeks.

*Plant height, soil level to top of flowers*.—About 50 cm.

*Plant height, soil level to top of leaves*.—About 5 cm.

*Plant diameters* (*longest by shortest*).—About 35 by 15 cm.

*Flowering stem*.—Length: About 50 cm. Diameter: About 6 mm. Texture: Smooth. Pseudobulbs: Not observed. Color: 200A, with very narrow (less than 0.1 mm) and short (less than 1 mm in length) light greenish brown stripes.

Foliage description:

*Arrangement*.—Single, distichous.

*Quantity of leaves per plant*.—About 6.

*Length*.—About 20 cm.

*Width*.—About 9 cm.

*Shape*.—Elliptic.

*Apex*.—Rounded.

*Base*.—Cuneate, sessile.

*Margin*.—Entire.

*Aspect*.—Initially erect, then horizontal to arching.

*Texture*.—Leathery, thick, fleshy and glabrous.

*Venation pattern*.—Parallel.

*Color*.—Young foliage, upper surface: 139A. Young foliage, lower surface: 70A. Mature foliage, upper surface: 139A; venation, 139A. Mature foliage, lower surface: 137A with random speckles, 70A, towards the margins; venation, 70A.

Flower description:

*Natural flowering season*.—January and February in Northern Europe.

*Flower arrangement*.—Single zygomorphic flowers arranged in terminal and axillary racemes.

*Flower quantity*.—Freely flowering; usually about 10 to 15 flowers and flower buds per raceme.

*Fragrance*.—None detected.

*Flower longevity*.—Excellect longevity on the plant, about 8 weeks; cut flowers last about 2 weeks. Flowers not persistent.

*Flowers*.—Height: About 7 cm. Diameter: About 9 cm. Depth: About 7 cm.

*Flower buds*.—Length: About 2.5 to 3.5 cm. Diameter: About 1.5 to 2 cm. Shape: Spherical. Color: 77A.

*Petals*.—Arrangement: Two lateral petals flanking a third central modified petal or labellum. Length: Lateral petals: About 5 cm. Labellum: About 3 cm. Width: Lateral petals: About 4 cm. Labellum: About 2.5 cm. Shape: Lateral petals: Broadly rounded or obovate; apex rounded with emarginate tendencies; slightly concave. Labellum: Saccate; deeply three-lobed. Lateral lobes are elliptic to rounded and fold upward around the gynandrium. The central lobe is triangular with two prominent callosities at the base and two filiform appendages at the apex. Margin: Entire. Texture: Slightly rugose. Color: Lateral petals: When opening, upper and lower surfaces: 80B to 80C; fading to almost white, close to 155D, towards the margins. Fully opened, upper and lower surfaces: 80C to 80D; fading to almost white, close to 155D, towards the margins. Labellum: Lateral lobes: Towards apex, 80B; towards base, 80D to 155D; spots, 80A. Central lobe: Towards apex, 80A; towards base, 80D. Callosities: 9A. Appendages: Distal, 155D; proximal, 80A.

*Sepals*.—Arrangement: Three in a single whorl. Length: About 7 cm. Width: About 7 cm. Shape: Elliptic to ovate; apex, rounded; uppermost sepal apex with emarginate tendencies; slightly concave. Margin: Entire. Texture: Slightly rugose. Color: Upper surface: 80B, fading towards the margins to 80C. Lower surface: 80A, fading towards margins to 80C.

*Pedicels*.—Length: About 4 to 5 cm. Angle: Perpendicular to stem. Strength: Very strong. Color: Proximal, 187A; distal, 80D.

*Reproductive organs*.—Stamens, style and stigma united into a gynandrium with one terminal anther above the stigmas with pollen grains united into a pollinia. Gynandrium length: About 9 to 10 mm. Gynandrium diameter: About 8 mm. Gynandrium color: 80B. Pollinia quantity: Two per flower. Pollinia length: About 1.2 mm. Pollinia shape: Oval. Pollinia color: 25B. Stigma length: About 4 to 5 mm. Stigma shape: Oval, concave. Stigma color: 84C. Style color: 80B fading to 80D. Ovary: Inferior, three-carpelled. Ovary length: About 1 to 1.2 cm. Ovary diameter: About 1.5 mm. Ovary color: Close to 155D to 150D.

*Seed*.—Seed production has not been observed.

Disease resistance: Resistance to known pathogens of Phalaenopsis has not been observed on plants grown under commercial production conditions.

Temperature tolerance: Plants of the new Phalaenopsis tolerate temperatures from 15 to 38° C.

It is claimed:

1. A new and distinct Phalaenopsis plant named 'Artemisa', as illustrated and described.

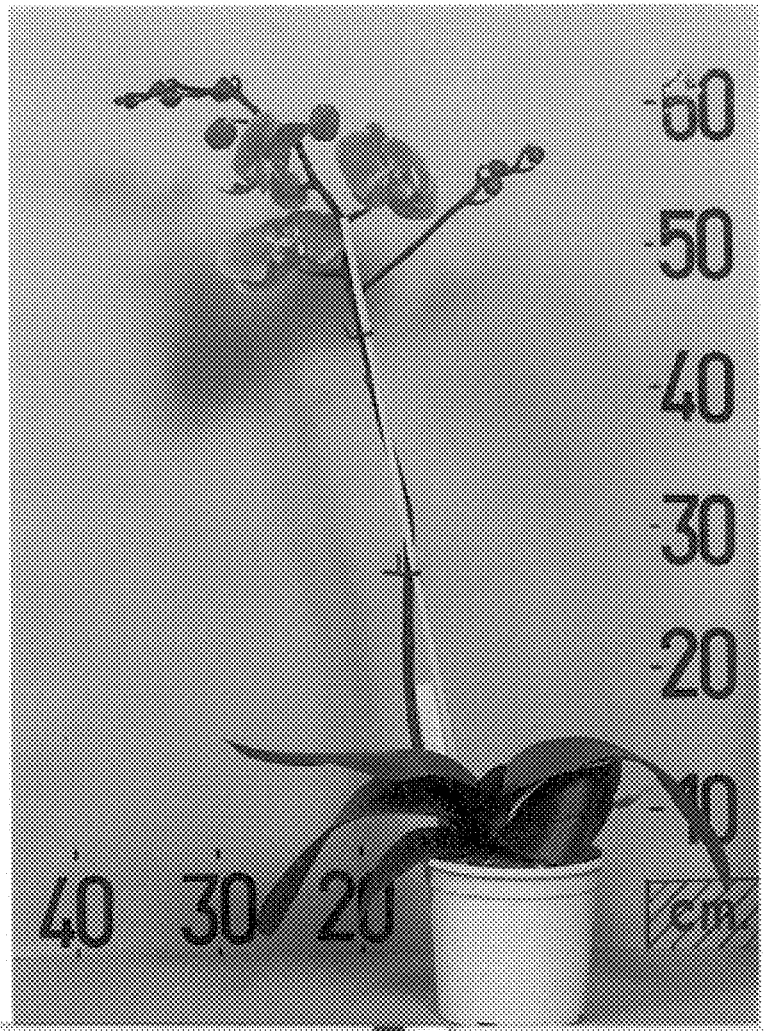
60
50
40
30
20
10
40 30 20
cm
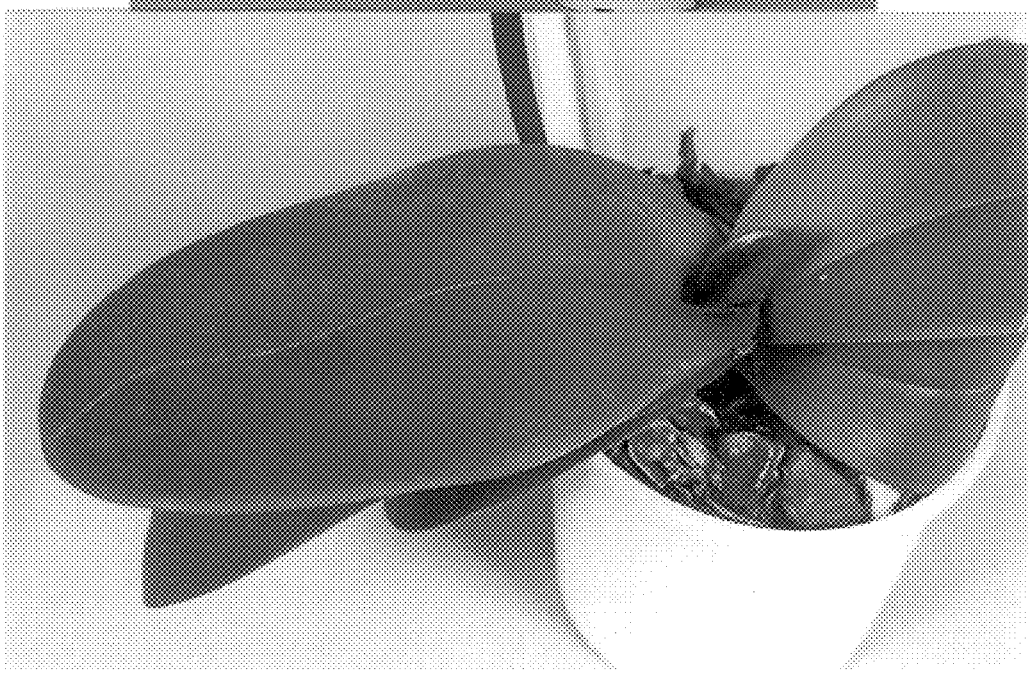

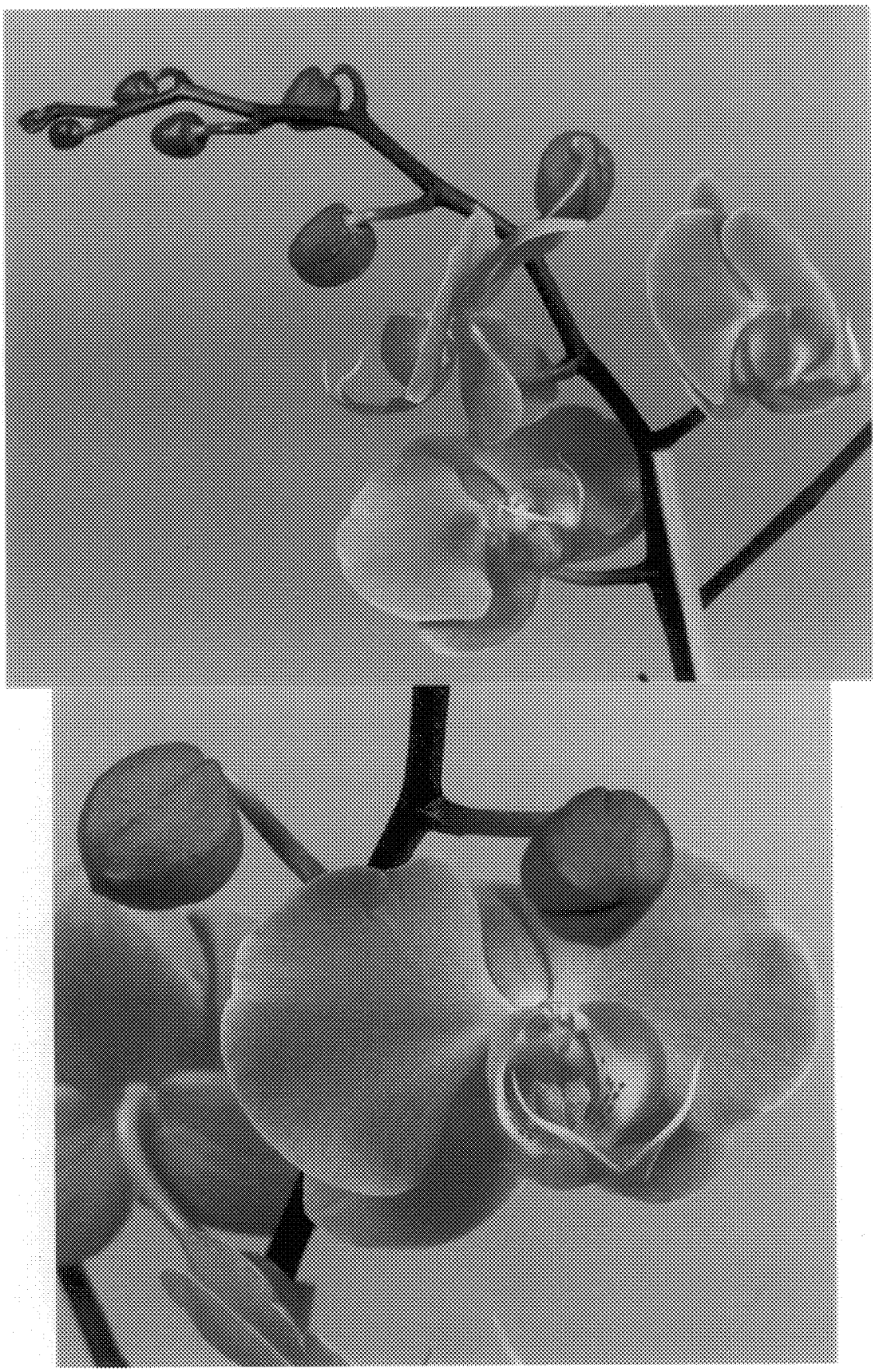

* * * * *